(12) United States Patent
Nakayama et al.

(10) Patent No.: US 11,515,949 B2
(45) Date of Patent: Nov. 29, 2022

(54) ESTIMATION METHOD AND DEVICE TO IDENTIFY NEXT POSITION OF A LIVING BODY

(71) Applicant: PANASONIC INTELLECTUAL PROPERTY MANAGEMENT CO., LTD., Osaka (JP)

(72) Inventors: Takeshi Nakayama, Hyogo (JP); Shoichi Iizuka, Osaka (JP); Naoki Honma, Iwate (JP); Dai Sasakawa, Kanagawa (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 434 days.

(21) Appl. No.: 16/708,724

(22) Filed: Dec. 10, 2019

(65) Prior Publication Data

US 2020/0213014 A1 Jul. 2, 2020

(30) Foreign Application Priority Data

Dec. 28, 2018 (JP) .............................. JP2018-247657
Sep. 2, 2019 (JP) .............................. JP2019-159506

(51) Int. Cl.
*A61B 5/05* (2021.01)
*H04B 13/00* (2006.01)
(Continued)

(52) U.S. Cl.
CPC ............. *H04B 13/005* (2013.01); *A61B 5/05* (2013.01); *G01S 13/34* (2013.01); *H04B 7/0697* (2013.01)

(58) Field of Classification Search
CPC ....... H04B 13/005; H04B 7/0697; H61B 5/05
See application file for complete search history.

(56) References Cited

U.S. PATENT DOCUMENTS

| 7,372,404 | B2 * | 5/2008 | Shirai | .................. | G01S 3/8006 |
| | | | | | 342/417 |
| 7,817,082 | B2 * | 10/2010 | Dwelly | .................. | G01S 7/415 |
| | | | | | 342/134 |

(Continued)

FOREIGN PATENT DOCUMENTS

| JP | 2002-267744 | 9/2002 |
| JP | 2015-085065 | 5/2015 |

(Continued)

OTHER PUBLICATIONS

Sasakawa et al., "Human Identification Using MIMO Array", Journal of Latex Class Files, vol. 14, No. 8, Aug. 2015, pp. 1-7.

(Continued)

*Primary Examiner* — Abdelnabi O Musa
(74) *Attorney, Agent, or Firm* — Greenblum & Bernstein, P.L.C.

(57) ABSTRACT

An estimation method includes: transmitting transmission signals using M transmission antenna elements; receiving reception signals by N reception antenna elements; calculating, from the reception signals, a first matrix whose components are complex transfer functions indicating propagation characteristics between the transmission antenna elements and the reception antenna elements; estimating, using the first matrix, a position and an orientation of a living body relative to an estimation device; when the estimated position is in a first identification region and the estimated orientation is in a predetermined range from a first direction, identifying the living body based on time waveforms of the reception signals and a first training signal which is obtained in advance in the first identification region and corresponds to the living body; and adding, as an identification region for identifying the first living body (Continued)

identified, a new identification region based on an estimated position of the first living body identified.

8 Claims, 11 Drawing Sheets

(51) Int. Cl.
  *G01S 13/34* (2006.01)
  *H04B 7/06* (2006.01)

(56) References Cited

U.S. PATENT DOCUMENTS

| | | | | |
|---|---|---|---|---|
| 8,890,684 | B2* | 11/2014 | Tkachenko | G01S 11/06 |
| | | | | 342/51 |
| 9,176,223 | B2* | 11/2015 | Derham | G01S 13/04 |
| 9,291,707 | B2* | 3/2016 | Nohara | G01S 13/726 |
| 10,241,187 | B2 | 3/2019 | Honma et al. | |
| 2013/0093616 | A1* | 4/2013 | Jeon | G01S 7/414 |
| | | | | 342/118 |
| 2015/0223733 | A1 | 8/2015 | Al-Alusi | |
| 2017/0082741 | A1 | 3/2017 | Adib et al. | |
| 2017/0184699 | A1* | 6/2017 | Honma | G01S 3/74 |
| 2017/0205502 | A1* | 7/2017 | Honma | G01S 13/46 |
| 2018/0011169 | A1 | 1/2018 | Nakayama et al. | |
| 2018/0192919 | A1 | 7/2018 | Nakayama et al. | |
| 2018/0196131 | A1* | 7/2018 | Iizuka | G01S 13/003 |
| 2019/0195997 | A1* | 6/2019 | Iizuka | H04B 7/0456 |

FOREIGN PATENT DOCUMENTS

| | | |
|---|---|---|
| JP | 2017-508149 | 3/2017 |
| JP | 2017-144132 | 8/2017 |
| JP | 2018-008021 | 1/2018 |
| JP | 2018-029671 | 3/2018 |
| JP | 2018-075406 | 5/2018 |
| JP | 2018-112540 | 7/2018 |
| JP | 2019-117055 | 7/2019 |
| WO | 2015/175078 | 11/2015 |

OTHER PUBLICATIONS

Shiraki et al., "Method of Estimating Human Orientation Using Array Antenna", Electronics, vol. 7, No. 92, 2018, pp. 1-9.

* cited by examiner

FIG. 4

| TRAINING DATA | | | | |
|---|---|---|---|---|
| LIVING BODY 50 | FIRST IDENTIFICATION REGION | FIRST TRAINING POSITION | | FIRST TRAINING SIGNAL |
| | | FIRST TRAINING ORIENTATION | | |
| | SECOND IDENTIFICATION REGION | SECOND TRAINING POSITION | | SECOND TRAINING SIGNAL |
| | | SECOND TRAINING ORIENTATION | | |
| | ... | | | |
| LIVING BODY 51 | FIRST IDENTIFICATION REGION | FIRST TRAINING POSITION | | FIRST TRAINING SIGNAL |
| | | FIRST TRAINING ORIENTATION | | |
| | ... | | | |
| ... | ... | | | |

FIG. 5

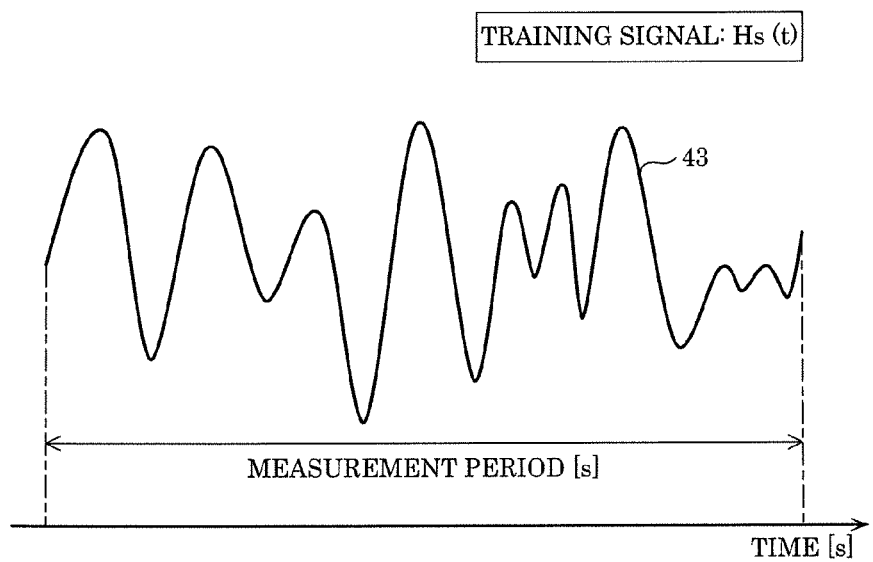

FIG. 11

| | | | | 42A |
|---|---|---|---|---|
| TRAINING DATA | | | | |
| LIVING BODY 50 | FIRST IDENTIFICATION REGION | FIRST TRAINING POSITION | | FIRST TRAINING SIGNAL |
| | | FIRST TRAINING ORIENTATION | | |
| | | FIRST TRAINING POSTURE | | |
| | SECOND IDENTIFICATION REGION | SECOND TRAINING POSITION | | SECOND TRAINING SIGNAL |
| | | SECOND TRAINING ORIENTATION | | |
| | | SECOND TRAINING POSTURE | | |
| | ... | | | |
| LIVING BODY 51 | FIRST IDENTIFICATION REGION | FIRST TRAINING POSITION | | FIRST TRAINING SIGNAL |
| | | FIRST TRAINING ORIENTATION | | |
| | | FIRST TRAINING POSTURE | | |
| | ... | | | |
| ... | | ... | | | ns
ESTIMATION METHOD AND DEVICE TO IDENTIFY NEXT POSITION OF A LIVING BODY

CROSS REFERENCE TO RELATED APPLICATION

This application claims the benefit of priorities of Japanese Patent Application Number 2018-247657 filed on Dec. 28, 2018 and Japanese Patent Application Number 2019-159506 filed on Sep. 2, 2019, the entire contents of which are hereby incorporated by reference.

BACKGROUND

1. Technical Field

The present disclosure relates to an estimation method and an estimation device for emitting radio signals to a living body and receiving reflected signals to identify the living body.

2. Description of the Related Art

A technique of emitting radio signals to a living body and receiving reflected signals to identify the living body is known (see Japanese Unexamined Patent Application Publication No. 2017-144132, for example). Japanese Unexamined Patent Application Publication No. 2017-144132 discloses a device that identifies the driver of a vehicle by emitting electromagnetic waves to the driver and extracting heartbeat and a heart sound signal using reflected waves. Non-Patent Literature 2 (Dai Sasakawa, Naoki Honma, Takeshi Nakayama, and Shoichi Iizuka, "Human Identification Using MIMO Array", IEEE SENSORS JOURNAL, VOL. 18, NO. 8, Apr. 15, 2018, URL: https://ieeexplore.ieee.org/document/8283708) discloses a method for identifying a living body using radio signals and antennas provided around the subject. Methods of emitting radio signals to a living body to estimate the position, orientation, and behavior of the living body are disclosed in Japanese Unexamined Patent Application Publication No. 2018-8021, Japanese Unexamined Patent Application Publication No. 2018-112540, Japanese Unexamined Patent Application Publication No. 2017-508149, and Japanese Unexamined Patent Application Publication No. 2018-29671.

Japanese Unexamined Patent Application Publication No. 2018-75406, for example, discloses a method for identifying an individual by using radar. Japanese Unexamined Patent Application Publication No. 2015-85065, for example, discloses a method for obtaining vital data and position tracking by using radar. Non-Patent Literature 1 (Nobuyuki Shiraki, Zhixiong Chen, Dai Sasakawa, Naoki Honma, Takeshi Nakayama, and Shoichi Iizuka, "Method of Estimating Human Orientation Using Array Antenna", URL: https://www.mdpi.com/2079-9292/7/6/92) discloses a method for estimating a person's orientation using radio signals, and Non-Patent Literature 2 discloses a method for human biometric identification using radio signals.

SUMMARY

As disclosed in Japanese Unexamined Patent Application Publication No. 2017-144132 or Non-Patent Literature 2, living body identification using electromagnetic waves is often performed in a state where the measurement subject and each antenna are relatively close to each other. When identifying an individual in a small space such as a driver's seat or a private room, the restriction that the distance between the subject and each antenna is short is not likely to be a problem, but such individual identification is not easy to use in daily life scenes, for example.

The present disclosure has been conceived in view of the above circumstances, and provides an estimation device and an estimation method capable of living body identification using electromagnetic waves even in a situation, for example, in an indoor space, where the subject and antennas are distant from each other.

To provide such an estimation device and an estimation method, an estimation method according to an aspect of the present disclosure is an estimation method for an estimation device which includes an antenna and memory, the antenna including M transmission antenna elements and N reception antenna elements, where M and N are each a natural number greater than or equal to two. The estimation method includes: transmitting transmission signals to a target region using the M transmission antenna elements; receiving, by the N reception antenna elements, reception signals which include one or more reflected signals resulting from one or more of the transmission signals transmitted by the M transmission antenna elements being reflected by a first living body; calculating, from N reception signals respectively received by the N reception antenna elements in a predetermined length of time, an M×N first matrix whose components are complex transfer functions each indicating a propagation characteristic between one of the M transmission antenna elements and one of the N reception antenna elements; successively estimating, using the first matrix calculated, combinations each of which is a combination of a position and an orientation of the first living body relative to the estimation device, in a time series that is an order in which the N reception signals are received; determining, for each of the combinations successively estimated, whether (i) the position of the first living body in the combination is in a first identification region which is included in the target region and stored in the memory in advance as an identification region and (ii) the orientation of the first living body in the combination is in a predetermined range relative to a direction stored in the memory in advance; identifying the first living body based on time waveforms of the reception signals and a first training signal which is obtained in advance in the first identification region and corresponds to a second living body, when (i) the position of the first living body in the combination is included in the first identification region and (ii) the orientation of the first living body in the combination is in the predetermined range; and adding a new identification region as the identification region for identifying the first living body identified, the new identification region being based on information indicating an estimated next position of the first living body identified.

An estimation method according to another aspect of the present disclosure is an estimation method for an estimation device which includes an antenna and memory, the antenna including M transmission antenna elements and N reception antenna elements, where M and N are each greater than or equal to three. The memory stores information indicating correspondence among (i) a change over time in a vertical position of the first living body in a vertical direction relative to the estimation device, (ii) a change over time in a radar cross-section (RCS) value, and (iii) an action of a first living body. The M transmission antenna elements include at least three transmission antenna elements disposed in different positions in the vertical direction and a horizontal direction. The N reception antenna elements include at least three reception antenna elements disposed in different positions in the vertical direction and the horizontal direction. The estimation method includes: transmitting transmission signals to a target region using the M transmission antenna elements; receiving, by the N reception antenna elements, reception signals which include one or more reflected signals resulting from one or more of the transmission signals transmitted by the M transmission antenna elements being reflected by a first living body; calculating, from N reception signals respectively received by the N reception antenna elements in a predetermined length of time, an M×N first matrix whose components are complex transfer functions each indicating a propagation characteristic between one of the M transmission antenna elements and one of the N reception antenna elements; successively estimating, using the first matrix calculated, combinations each of which is a combination of a three-dimensional position and an orientation of the first living body relative to the estimation device, in a time series that is an order in which the N reception signals are received, the three-dimensional position including the vertical position; successively calculating, for each of three-dimensional positions successively estimated, an RCS value corresponding to the first living body based on the three-dimensional position, positions of the M transmission antenna elements, and positions of the N reception antenna elements; successively estimating a posture of the first living body for each of the combinations, using (i) a change over time in the three-dimensional positions successively estimated, (ii) a change over time in RCS values successively calculated, and (iii) the information indicating the correspondence stored in the memory; determining, for each of the combinations successively estimated, whether (i) the three-dimensional position in the combination is in a first identification region which is included in the target region and stored in the memory in advance as an identification region, (ii) the orientation of the first living body in the combination is in a predetermined range relative to a first direction stored in the memory in advance, and (iii) the posture of the first living body in the combination matches a first posture stored in the memory in advance; identifying the first living body based on time waveforms of the reception signals and a first training signal which is obtained in advance in the first identification region and corresponds to a second living body, when (i) the three-dimensional position of the first living body in the combination is in the first identification region, (ii) the orientation of the first living body in the combination is in the predetermined range, and (iii) the posture of the first living body in the combination matches the first posture; and adding a new identification region as the identification region for identifying the first living body identified, the new identification region being based on information indicating an estimated next position of the first living body identified.

Note that these general or specific aspects may be implemented by a system, a device, an integrated circuit, a computer program, or a non-transitory computer-readable recording medium such as a compact disc read only memory (CD-ROM), or by any combination of systems, devices, integrated circuits, computer programs, or recording media.

An estimation device and an estimation method according to the present disclosure are capable of living body identification using electromagnetic waves even in a situation, for example, in an indoor space, where the subject and antennas are distant from each other.

BRIEF DESCRIPTION OF DRAWINGS

These and other objects, advantages and features of the disclosure will become apparent from the following description thereof taken in conjunction with the accompanying drawings that illustrate a specific embodiment of the present disclosure.

FIG. 4 illustrates an example of training data stored in memory according to Embodiment 1;

FIG. 5 illustrates an example of a training signal included in training data illustrated in FIG. 1;

FIG. 11 illustrates an example of training data stored in memory according to Embodiment 2.

DETAILED DESCRIPTION OF THE EMBODIMENTS

Figure 1:
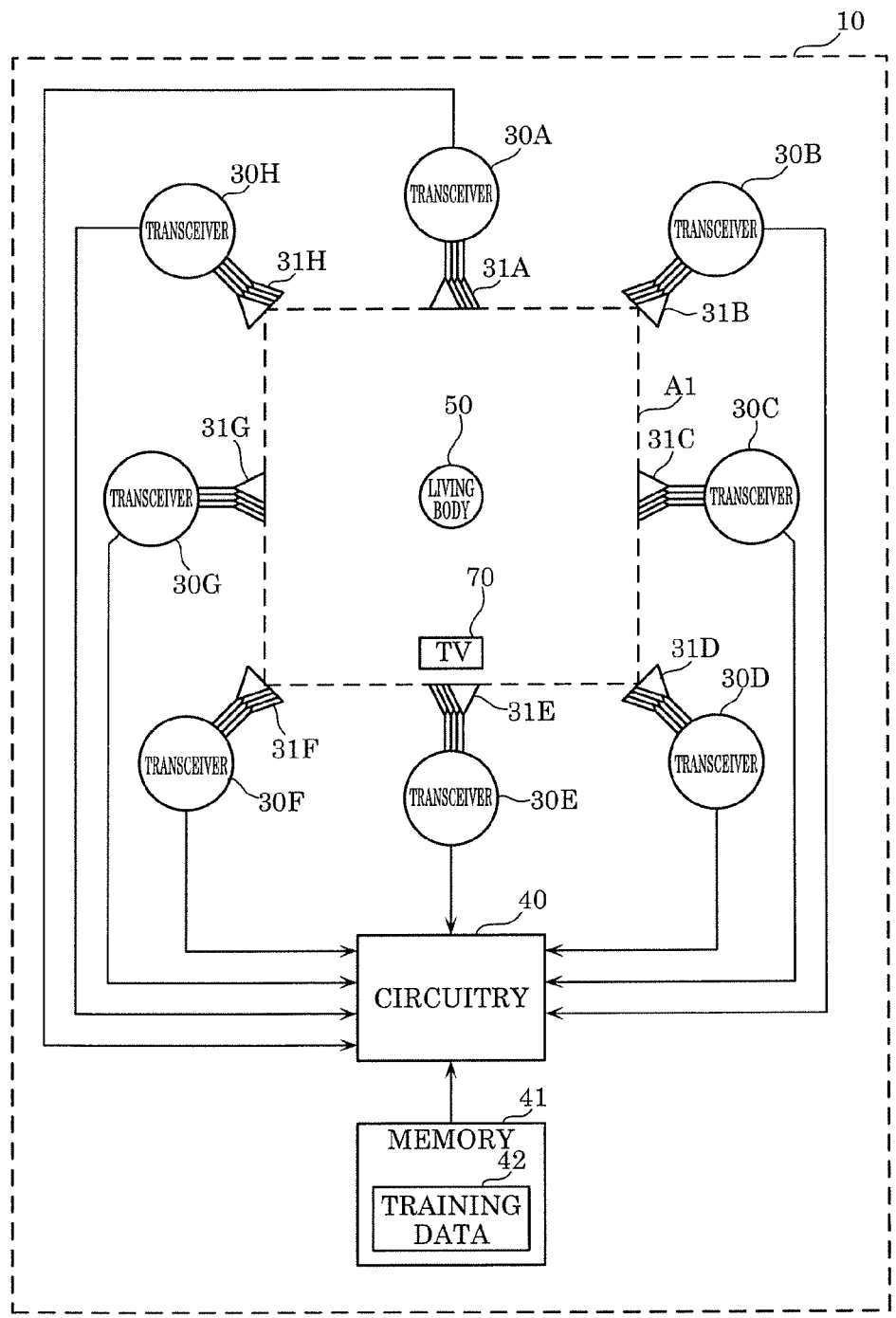
FIG. 1 is a configuration diagram illustrating an example of a configuration of an estimation device according to Embodiment 1.

Underlying Knowledge Forming Basis of the Present Disclosure

Japanese Unexamined Patent Application Publication No. 2017-144132 emits electromagnetic waves to a person in the driver's seat of a vehicle, and measures reflected waves reflected by the person. Then, the heartbeat or heart sound is measured by performing arithmetic processing on the measurement result, and time correlation of the measured heartbeat or heart sound is obtained so as to achieve living body identification. However, as described above, the method disclosed in Japanese Unexamined Patent Application Publication No. 2017-144132 has a problem that it can be used only in a limited environment where the positions of the subject and an antenna can be specified in a narrow space such as the driver's seat. For this reason, what is desired is identification of an individual in an environment, for example, in indoor daily life scenes, where the antenna and the subject are distant from each other and where the antenna and the subject are flexible in their positional relationship.

As a result of repeated researches for addressing this problem, the inventors have found the following to be able to perform living body identification using electromagnetic waves even in a situation, for example, in an indoor space, where the subject and antennas are distant from each other. More specifically, antenna elements are disposed around a room where the subject performs an activity, transmission waves are transmitted from various directions, and reflected waves and scattered waves are received in various directions, so as to obtain reception signals indicating many characteristics of the living body. The reception signals significantly change depending on the direction and posture of the living body and the distance between the living body and the antennas. Thus, in order to identify the living body, training data is obtained while estimating the position, orientation, and posture of the living body from the reception signals, and the position, orientation, and posture of the living body are stored as an identification region. The inventors have found that by calculating a correlation with the training data when the subject takes the same position, orientation, posture as those indicated by the identification region, it is possible to precisely identify whether a signal indicating the target living body is included in the training data even in a region such as a living space.

More specifically, to provide such an estimation device and an estimation method as described above, an estimation method according to an aspect of the present disclosure is an estimation method for an estimation device which includes an antenna and memory, the antenna including M transmission antenna elements and N reception antenna elements, where M and N are each a natural number greater than or equal to two. The estimation method includes: transmitting transmission signals to a target region using the M transmission antenna elements; receiving, by the N reception antenna elements, reception signals which include one or more reflected signals resulting from one or more of the transmission signals transmitted by the M transmission antenna elements being reflected by a first living body; calculating, from N reception signals respectively received by the N reception antenna elements in a predetermined length of time, an M×N first matrix whose components are complex transfer functions each indicating a propagation characteristic between one of the M transmission antenna elements and one of the N reception antenna elements; successively estimating, using the first matrix calculated, combinations each of which is a combination of a position and an orientation of the first living body relative to the estimation device, in a time series that is an order in which the N reception signals are received; determining, for each of the combinations successively estimated, whether (i) the position of the first living body in the combination is in a first identification region which is included in the target region and stored in the memory in advance as an identification region and (ii) the orientation of the first living body in the combination is in a predetermined range relative to a direction stored in the memory in advance; identifying the first living body based on time waveforms of the reception signals and a first training signal which is obtained in advance in the first identification region and corresponds to a second living body, when (1) the position of the first living body in the combination is included in the first identification region and (ii) the orientation of the first living body in the combination is in the predetermined range; and adding a new identification region as the identification region for identifying the first living body identified, the new identification region being based on information indicating an estimated next position of the first living body identified.

With this, when a living body is identified in the position in the first identification region that has been previously stored in the memory and in the orientation in the predetermined range that has been previously stored in the memory, and then moves to a position outside the first identification region, a new identification region which is based on the position to which the living body has moved is added as an identification region for identifying the identified first living body. Accordingly, next time when the living body is to be identified, it is possible to identify the first living body not only in the first identification region but also in the new identification region, thus enabling efficient identification of the first living body.

The adding of the new identification region may include: (i) continuing to track, at predetermined time intervals, the position of the first living body identified, based on a result of the estimating; (ii) when the first living body remains still for a predetermined period or longer in a second identification region different from the first identification region, generating a second training signal corresponding to the second identification region based on reception signals received in the predetermined period and a position and an orientation of the first living body estimated using the reception signals; and (iii) adding the second training signal as a training signal for identifying, in the second identification region, the first living body identified, and in the identifying of the first living body, the first living body in the first identification region is identified using the first training signal, and the first living body in the second identification region is identified using the second training signal. With this, since the first living body in the second identification region can be identified using the second training signal, the first living body can be identified both in the first identification region and the second identification region. Accordingly, next time when the first living body is to be identified, it is possible to efficiently identify the first living body.

The estimation method may further include identifying the first living body based on (i) time waveforms of the reception signals and (ii) the first training signal and the second training signal which are obtained in advance in the first identification region or the second identification region and correspond to a second living body, when the first living body is estimated to have remained still for the predetermined period or longer in the first identification region or the second identification region based on the result of the estimating.

An estimation method according to another aspect of the present disclosure is an estimation method for an estimation device which includes an antenna and memory, the antenna including M transmission antenna elements and N reception antenna elements, where M and N are each greater than or equal to three. The memory stores information indicating correspondence among (i) a change over time in a vertical position of the first living body in a vertical direction relative to the estimation device, (ii) a change over time in a radar cross-section (RCS) value, and (iii) an action of a first living body. The M transmission antenna elements include at least three transmission antenna elements disposed in different positions in the vertical direction and a horizontal direction. The N reception antenna elements include at least three reception antenna elements disposed in different positions in the vertical direction and the horizontal direction. The estimation method includes: transmitting transmission signals to a target region using the M transmission antenna elements; receiving, by the N reception antenna elements, reception signals which include one or more reflected signals resulting from one or more of the transmission signals transmitted by the M transmission antenna elements being reflected by a first living body; calculating, from N reception signals respectively received by the N reception antenna elements in a predetermined length of time, an M×N first matrix whose components are complex transfer functions each indicating a propagation characteristic between one of the M transmission antenna elements and one of the N reception antenna elements; successively estimating, using the first matrix calculated, combinations each of which is a combination of a three-dimensional position and an orientation of the first living body relative to the estimation device, in a time series that is an order in which the N reception signals are received, the three-dimensional position including the vertical position; successively calculating, for each of three-dimensional positions successively estimated, an RCS value corresponding to the first living body based on the three-dimensional position, positions of the M transmission antenna elements, and positions of the N reception antenna elements; successively estimating a posture of the first living body for each of the combinations, using (i) a change over time in the three-dimensional positions successively estimated, (ii) a change over time in RCS values successively calculated, and (iii) the information indicating the correspondence stored in the memory; determining, for each of the combinations successively estimated, whether (i) the three-dimensional position in the combination is in a first identification region which is included in the target region and stored in the memory in advance as an identification region, (ii) the orientation of the first living body in the combination is in a predetermined range relative to a first direction stored in the memory in advance, and (iii) the posture of the first living body in the combination matches a first posture stored in the memory in advance; identifying the first living body based on time waveforms of the reception signals and a first training signal which is obtained in advance in the first identification region and corresponds to a second living body, when (i) the three-dimensional position of the first living body in the combination is in the first identification region, (ii) the orientation of the first living body in the combination is in the predetermined range, and (iii) the posture of the first living body in the combination matches the first posture; and adding a new identification region as the identification region for identifying the first living body identified, the new identification region being based on information indicating an estimated next position of the first living body identified.

With this, when a living body is identified in the position in the first identification region that has been previously stored in the memory, in the orientation in the predetermined range that has been previously stored in the memory, and in the first posture that has been previously stored in the memory, and then moves to a position outside the first identification region, a new identification region which is based on the position to which the living body has moved is added as an identification region for identifying the identified first living body. Accordingly, next time when the living body is to be identified, it is possible to identify the first living body not only in the first identification region but also in the new identification region, thus enabling efficient identification of the first living body.

The adding of the new identification region may include: (i) continuing to track, at predetermined time intervals, the position of the first living body identified, based on a result of the estimating; (ii) when the first living body remains still for a predetermined period or longer in at least one second identification region different from the first identification region, generating a second training signal corresponding to the at least one second identification region based on the reception signals received in the predetermined period and a three-dimensional position, an orientation, and a posture of the first living body estimated using the reception signals; and (iii) storing the second training signal in the memory as a training signal for identifying, in the at least one second identification region, the first living body identified, and in the identifying of the first living body, the first living body in the first identification region may be identified using the first training signal, and the first living body in the at least one second identification region may be identified using the second training signal.

With this, since the first living body in the second identification region can be identified using the second training signal, the first living body can be identified both in the first identification region and the second identification region. Accordingly, next time when the first living body is to be identified, it is possible to efficiently identify the first living body.

The estimation method may further include identifying the first living body based on (i) the time waveforms of the reception signals and (ii) the first training signal and the second training signal which are obtained in advance in the first identification region or the at least one second identification region and correspond to a second living body, when the first living body is estimated to have remained still for the predetermined period or longer in the first identification region or the second identification region based on the result of the estimating.

Note that these general or specific aspects may be implemented by a system, a device, an integrated circuit, a computer program, or a non-transitory computer-readable recording medium such as a CD-ROM, or by any combination of systems, methods, integrated circuits, computer programs, or recording media.

Hereinafter, exemplary embodiments of the present disclosure will be described in detail with reference to the drawings. Note that each of the exemplary embodiments described below illustrates a specific example of the present disclosure. The numerical values, shapes, materials, components, the arrangement and connection of the components, steps, the processing order of the steps, etc., shown in the following exemplary embodiments are mere examples, and are therefore not intended to limit the present disclosure. Furthermore, among the components in the following exemplary embodiments, those not recited in any one of the independent claims defining the broadest concept of the present disclosure are described as optional components making up a more preferable form. It should be noted that in the specification and the drawings, components having substantially the same functional configuration are given the same numerical sign in order to omit overlapping descriptions.

Embodiment 1

[Configuration of Estimation Device 10]

Figure 2:
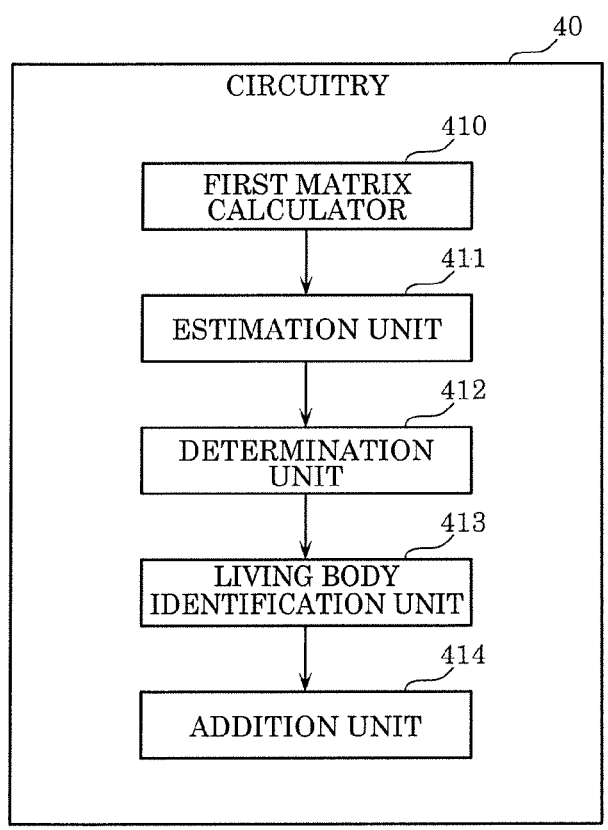
FIG. 2 is a configuration diagram illustrating an example of a detailed configuration of circuitry illustrated in FIG. 1.

FIG. 1 is a configuration diagram illustrating an example of a configuration of estimation device 10 according to the present embodiment. FIG. 2 is a configuration diagram illustrating an example of a detailed configuration of circuitry 40 illustrated in FIG. 1.

Estimation device 10 according to the present disclosure includes: transceivers 30A to 30H which include antenna elements 31A to 31H, respectively; circuitry 40; and memory 41. In transceivers 30A to 30H, a total number of transmission antenna elements is M and a total number of reception antenna elements is N, where each of M and N is a natural number greater than or equal to two.

Transceivers 30A to 30H are disposed in two or more positions (eight in the present embodiment). In the present embodiment, assuming predetermined region A1 as a square room of six meters by six meters in a plan view, transceivers 30A to 30H are disposed in eight positions including the four corners of predetermined region A1 and the centers of the four sides of predetermined region A1. Each of transceivers 30A to 30H includes an array antenna of four antenna elements that are horizontally arranged. This means, 32 transmission antenna elements and 32 reception antenna elements are disposed around predetermined region A1. Note that the above is a mere example of the arrangement of the array antennas; the array antennas may be disposed only in the four corners of predetermined region A1, or may be disposed only on the four sides of predetermined region A1, or may be disposed on any of the four sides as well as the corners at both ends of that side, for example. Moreover, the transmission antenna elements and reception antenna elements may be disposed in the same position or may be disposed in different positions. In other words, the array antennas may be disposed in any manner, so long as they are disposed in two or more different positions to surround predetermined region A1.

The M transmission antenna elements transmit transmission signals to predetermined region A1 in which living body 50 is present. The transmission signals are high frequency signals such as microwaves generated by a transmitter, for example. Living body 50 is a human, for example. Living body 50 is a subject of identification by estimation device 10, and is a subject of biometric authentication. Predetermined region A1 is a space of a predefined area, and is a space in which living body 50 is present. Predetermined region A1 is a target region for identifying living body 50.

The M transmission antenna elements, for example, transmit first transmission signals to predetermined region A1 in which a first living body, i.e., living body 50 to be measured, is present. The M transmission antenna elements also transmit second transmission signals to predetermined region A1 in which a second living body, i.e., known living body 50 serving as training data, is present.

Transceivers 30A to 30H receive, in a predetermined length of time, reception signals that are respectively received by the N reception antenna elements. The reception signals include one or more reflected signals resulting from one or more of the transmission signals respectively transmitted by the M transmission antenna elements being reflected by living body 50. For example, using reception antenna elements included in transceivers 30A to 30H, transceivers 30A to 30H receive, in a predetermined length of time, first reception signals which include one or more reflected signals resulting from one or more of first transmission signals being reflected by a first living body. Furthermore, for example, using the reception antenna elements included in transceivers 30A to 30H, transceivers 30A to 30H receive, in a period that is K times greater than the predetermined length of time, a first training signal which includes second reception signals including one or more reflected signals resulting from one or more of the second transmission signals being reflected by a second living body, where K is greater than or equal to two.

As illustrated in FIG. 1, estimation device 10 in the present embodiment includes eight transceivers 30A to 30H, circuitry 40, and memory 41, for example. In other words, the M transmission antenna elements and the N reception antenna elements may be configured of antenna elements 31A to 31H included in eight transceivers 30A to 30H. Note that the total number of transceivers is not limited to eight.

[Transceivers 30A to 30H]

In the present embodiment, eight transceivers 30A to 30H are disposed in positions surrounding predetermined region A1, and transmit transmission signals to predetermined region A1 in which living body 50 such as a human is present, so as to receive reception signals including one or more reflected signals reflected by living body 50. For example, eight transceivers 30A to 30H may be disposed in a circle at equal intervals, or may be disposed at the corners of predetermined region A1 and/or the centers of the sides of predetermined region A1.

As illustrated in FIG. 1, transceivers 30A to 30H include four antenna elements 31A to 31H, respectively. Transceivers 30A to 30H transmit transmission signals to predetermined region A1 using antenna elements 31A to 31H. More specifically, transceivers 30A to 30H emit microwaves as transmission signals to living body 50 such as a human, using antenna elements 31A to 31H. Note that transceivers 30A to 30H may transmit, using antenna elements 31A to 31H, unmodulated transmission signals or transmission signals which have undergone modulation processing. In the case of transmitting transmission signals which have undergone modulation processing, transceivers 30A to 30H may further include circuitry for performing modulation processing.

Using antenna elements 31A to 31H, transceivers 30A to 30H receive, in a predetermined length of time, reception signals which include one or more reflected signals resulting from one or more of the transmission signals being reflected by living body 50. Transceivers 30A to 30H output the received reception signals to circuitry 40. Note that each of transceivers 30A to 30H may include circuitry for processing the reception signals. In such a case, each of transceivers 30A to 30H may perform frequency transform on the received reception signals into low frequency signals. Each of transceivers 30A to 30H may perform demodulation processing on the reception signals. Each of transceivers 30A to 30H then outputs, to circuitry 40, the signals resulting from the frequency transform and/or demodulation processing.

Note that although FIG. 1 illustrates an example where transmitters and receivers are configured of eight transceivers 30A to 30H each including four antenna elements used for both transmission and reception of signals, the present disclosure is not limited to this example. The total number of transceivers 30A to 30H is not limited to eight, and may be greater than or equal to two. Moreover, transmitters which include transmission antenna elements may be provided separately from receivers which include reception antenna elements. Although it has been stated above that one transceiver includes four antenna elements used for both of transmission and reception, one transceiver may include four transmission antenna elements and four reception antenna elements. Furthermore, although it has been stated above that each transceiver includes four antenna elements, the total number of antenna elements included in each transceiver is not limited to four, so long at least two antenna elements are included in each transceiver.

Note that although FIG. 1 illustrates an example where estimation device 10 includes eight transceivers 30A to 30H and one circuitry 40, the configuration of estimation device 10 is not limited to this, and estimation device 10 may include one circuitry 40 for each transceiver. In such a case of including more than one circuitry 40, subsequent-stage processing performed by more than one circuitry 40 may be performed through distributed processing.

[Circuitry 40]

Circuitry 40 implements various types of processing that operates estimation device 10. For example, circuitry 40 includes a processor that executes a control program, and a volatile storage area (a primary storage device) used as a work area for when executing the control program. The storage area is, for example, random access memory (RAM).

Circuitry 40 temporarily stores, in the storage area for a predetermined length of time, first reception signals respectively obtained from the N reception antenna elements. Circuitry 40 may temporarily store the phases and amplitudes of the first reception signals in the storage area for a predetermined length of time. In the present embodiment, circuitry 40 temporarily stores, in the storage area for a predetermined length of time, reception signals respectively obtained from transceivers 30A to 30H.

Note that circuitry 40 may include dedicated circuitry for performing various types of processing that operates estimation device 10. In other words, circuitry 40 may be circuitry that performs software processing, and may be circuitry that performs hardware processing. Circuitry 40 may include a nonvolatile storage area.

Next, a functional configuration of circuitry 40 will be described.

As illustrated in FIG. 2, circuitry 40 includes first matrix calculator 410, estimation unit 411, determination unit 412, living body identification unit 413, and addition unit 414.

[First Matrix Calculator 410]

First matrix calculator 410 transmits a known signal for complex transfer function measurement, using the M transmission antenna elements. First matrix calculator 410 then performs estimation by dividing the reception signals respectively received by the N reception antenna elements by the known signal.

More specifically, at first, first matrix calculator 410 calculates first matrix H(t) using the reception signals and the known signal stored in memory 41.

Here, first matrix H(t) obtained when a multiple-input and multiple-output (MIMO) array antenna of $M_r$ reception antenna elements and $M_t$ transmission antenna elements is disposed around predetermined region A1 is represented as Equation 1 below.

[Math. 1]

$$H(t) = \begin{pmatrix} h_{11}(t) & \cdots & h_{1M_t}(t) \\ \vdots & \ddots & \vdots \\ h_{M_r1}(t) & \cdots & h_{M_rM_t}(t) \end{pmatrix} \quad \text{(Equation 1)}$$

In Equation 1, $h_{ij}$ represents a complex channel response from the j-th transmitter to the i-th receiver, and t represents observation time.

In such a manner, first matrix calculator 410 calculates, from N reception signals respectively received by the N reception antenna elements in a predetermined length of time, an M×N first matrix whose components are complex transfer functions each indicating a propagation characteristic between one of the M transmission antenna elements and one of the N reception antenna elements. That is to say, first matrix calculator 410 calculates, for each of M×N possible antenna element combinations of one of the M transmission antenna elements and one of the N reception antenna elements, a complex transfer function indicating a propagation characteristic between the transmission antenna element and the reception antenna element in the combination, using the N reception signals observed in transceivers 30A to 30H in the predetermined length of time, so as to calculate an M×N complex transfer function matrix as the M×N first matrix.

<Estimation Unit 411>

Using the calculated first matrix, estimation unit 411 successively estimates combinations each of which is a combination of a position and an orientation of a living body relative to estimation device 10, in a time series that is the order in which the N reception signals are received. Estimation unit 411, for example, refers to the calculated first matrix and uses a method etc. disclosed in Japanese Unexamined Patent Application Publication No. 2018-8021 or Non-Patent Literature 1 so as to estimate the position and orientation of the living body present in predetermined region A1.

<Determination Unit 412>

Determination unit 412 determines, for each of the successively estimated combinations, whether (i) the position of the living body in the combination is in a first identification region which is included in predetermined region A1 and stored in memory 41 in advance as an identification region and (ii) the orientation of the living body in the combination is in a predetermined range relative to a direction stored in memory 41 in advance. Specifically, determination unit 412 refers to the first identification region indicated in training data 42 stored in memory 41, to refer to a first training position and a first training orientation of the living body that are associated with a first training region in the first identification region referred to. Here, the first identification region is information in which (i) the first training signal, (ii) the first training position and the first training orientation which are the position and orientation of the living body at the time of reception of the first training signal, respectively, and (iii) identification information (living body ID) that identifies the living body, are associated with one another. The identification information is, for example, an identification number, a character string, or the like, that uniquely identifies the living body. For example, determination unit 412 sets, as the condition of the first identification region, a condition that (i) the position of the living body is in a range of ±25 cm relative to the first training position serving as the standard and (ii) the orientation of the living body is in a range of ±20 degrees relative to the first training orientation serving as the standard. Determination unit 412 then determines whether an estimated position and an estimated orientation of the living body present in predetermined region A1 that are obtained by estimation unit 411 satisfy the condition of the first identification region for a first determination period or longer, e.g., five seconds or longer.

Here, the first determination period is not limited to five seconds or longer; it may be longer than five seconds in the case where further improvement is desired in reliability, or may be shorter than five seconds in the case of performing the determination in a shorter period. Moreover, the range for the position indicated in the first identification region is not limited to the range of ±25 cm relative to the standard position, and the range for the orientation indicated in the first identification region is not limited to the range of ±20 degrees relative to the standard orientation. Needless to say, the time period, the range for the position, or the range for the orientation may be increased or decreased, depending on the requirements for the application.

<Living Body Identification Unit 413>

When determination unit 412 determines that the living body satisfies the condition of the first identification region, living body identification unit 413 performs living body identification based on the time waveforms of the reception signals and the first training signal which is obtained in advance under the condition of the first identification region and corresponds to the living body, using a method etc. disclosed in Non-Patent Literature 2, for example. Specifically, living body identification unit 413 identifies the first living body by calculating correlation coefficients from the training signal and M×N reception signals obtained by receiving the reception signals, and determining whether the first living body and a second living body are identical using the calculated correlation coefficients. Living body identification unit 413 specifies the identification information that identifies the living body associated with the first training signal corresponding to the first identification region stored in memory 41, and outputs or stores in memory 41 the result of the living body identification.

When the training data stored in memory 41 already includes a plurality of training signals corresponding to a plurality of second living bodies for the same first training position and first training orientation, living body identification unit 413 may perform the living body identification for each of the training signals. In such a case, living body identification unit 413 identifies the first living body as a second living body determined to be identical to the first living body, among the plurality of second living bodies.

<Addition Unit 414>

Addition unit 414 adds, as the identification region for identifying the first living body identified, a new identification region which is based on information indicating an estimated next position of the first living body identified. With this, a new second identification region is added to training data 42 in memory 41 as the identification region for identifying the first living body. Specifically, once the living body identification is performed on the living body by living body identification unit 413, living body addition unit 414 continues tracking the living body based on plural estimation results obtained by estimation unit 411 at regular intervals, e.g., 0.5-second intervals. For example, addition unit 414 may track the living body by generating a movement trajectory of the living body based on the plural estimation results.

Furthermore, when the living body remains still for a second determination period or longer under the condition of the second identification region different from the first identification region, addition unit 414 generates a second training signal corresponding to the second identification region based on (i) the reception signals received in the second determination period and (ii) a second training position and a second training orientation which are the position and the orientation of the living body estimated using the reception signals. The second training signal has a waveform different from the waveform of the first training signal. Specifically, addition unit 414 performs processing using the result of determination by determination unit 412 indicating whether the living body has remained still for the second determination period or longer, e.g., five seconds or longer, in a position and an orientation different from the first training position and/or the first training orientation that serve as the standard for the condition of the first identification region. The second determination period may be the same as or different from the first determination period. When determination unit 412 determines that the living body which has undergone the living body identification remained still in the above-described position and orientation for the second determination period or longer, addition unit 414 determines the position as a second training position and the orientation as a second training orientation, and generates second training data by associating the living body with the second training position, the second training orientation, and the second training signal which includes the reception signals obtained in the second determination period. Note that the second determination period is not limited to five seconds, and may be a period of 10 seconds, 15 seconds, etc., for example.

After that, addition unit 414 stores the generated second training data in memory 41. That is to say, addition unit 414 adds the generated second training signal to memory 41 as a training signal for identifying the identified living body in the second identification region.

With this, next time when the first living body is to be identified, in the case where the first living body is estimated to have remained still for a predetermined period or longer under the condition of the first identification region or the second identification region based on the result of estimation by estimation unit 411, living body identification unit 413 can identify the first living body based on (i) the time waveforms of the reception signals and (ii) the first training signal and the second training signal which are obtained in advance under the condition of the first identification region or the second identification region and which correspond to the second living body.

Figure 3:
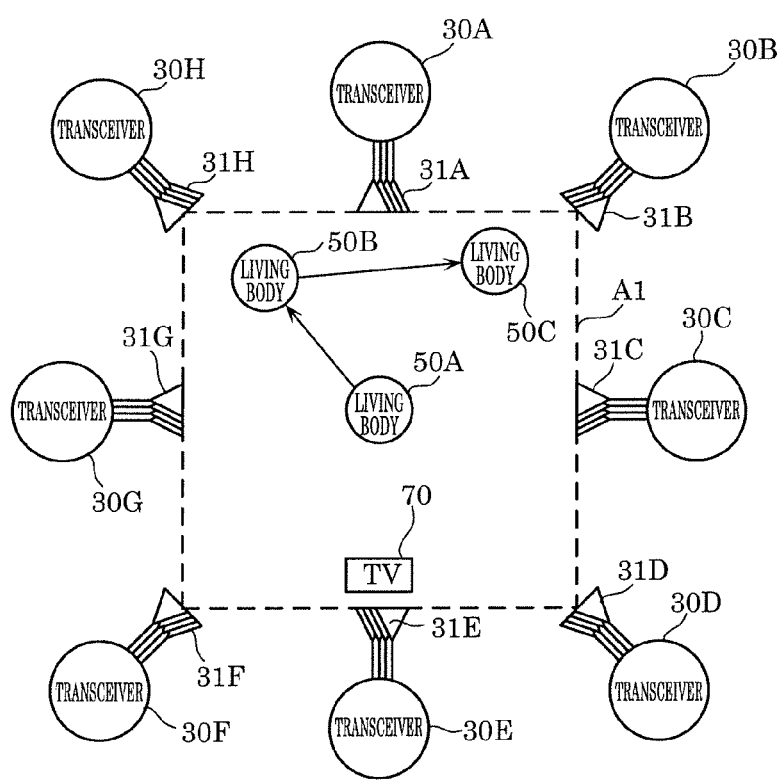
FIG. 3 illustrates an example of movement of a subject according to Embodiment 1.

A specific example will be described with reference to FIG. 3. FIG. 3 illustrates an environment used for an identification test performed by estimation device 10 according to the present embodiment. The details of the identification test will be described later.

Estimation device 10 first performs living body identification when a living body in FIG. 3 is present in position 50A. When the living body moves to position 50B and remains still in position 50B for the second determination period or longer, addition unit 414 tracks the movement trajectory of the living body from position 50A to position 50B, and recognizes the tracked living body as the living body which has undergone the living body identification. Then, because position 50B in which the living body remained still for the second determination period or longer does not satisfy the condition of the first identification region, addition unit 414 of estimation device 10 stores in memory 41, as training data, (i) position 50B, (ii) the orientation of the living body in position 50B, (iii) a training signal obtained in the second determination period since the living body has become still in position 50B, and (iv) identification information of the living body previously identified, when the living body remained still for the second determination period or longer. When the living body moves from position 50B to position 50C and remains still in position 50C for the second determination period or longer, addition unit 414 of estimation device 10 performs the same processing as the processing performed when the living body remained still in position 50B for the second determination period or longer.

[Memory 41]

Memory 41 is an auxiliary storage device which includes a non-volatile storage area, and is, for example, read only memory (ROM), flash memory, or a hard disk drive (HDD). For example, memory 41 stores information used in the various types of processing that operates estimation device 10.

As illustrated in FIG. 1, memory 41 stores training data 42. Training data 42 represents the signal waveforms of reception signals obtained in advance in relation to known living body 50 which is being still in a given position and orientation in predetermined region A1. Specifically, as illustrated in FIG. 4, training data 42 is information which includes identification information that identifies a living body, an identification region, and a training signal, and is information in which the identification information, the identification region, and the training signal are associated with one another. FIG. 4 illustrates an example of the training data stored in memory 41.

The identification region includes a training position and a training orientation. The identification region may include a predetermined range of region relative to the training position and a predetermined range of orientation relative to the training orientation. The identification region is specified based on the training position and the training orientation serving as the standard, and is used for deciding a condition of the determination performed by determination unit 412.

The training signal represents the signal waveforms of reception signals obtained when the position and orientation of the living body satisfy the condition specified by a corresponding identification region for the first determination period or longer or the second determination period or longer. When any one of the living body, the position of the living body, and the orientation of the living body changes, reception signals having different signal waveforms are obtained. Thus, when any one of the living body, the position of the living body, and the orientation of the living body changes, the training signal has a different signal waveform. Accordingly, when the position of the first living body, the orientation of the first living body, and the reception signals match the identification region and the training signal included in the training data, estimation device 10 can estimate that the first living body is identical to a second living body indicated in the identification information associated with the matching identification region and training signal.

The training signal includes M×N second reception signals obtained by causing the N reception antenna elements to receive in advance the second reception signals which include one or more reflected signals resulting from one or more of the second transmission signals transmitted to the second living body by the M transmission antenna elements being reflected by the second living body. Here, the training signal may include M×N second reception signals obtained by N receivers receiving the second reception signals in advance in a period that is K times greater than the predetermined length of time, where K is greater than or equal to two.

In the present embodiment, the M transmission antenna elements and the N reception antenna elements make up eight transceivers 30A to 30H as illustrated in FIG. 1. An example of the training signal in this case will be described with reference to FIG. 5. FIG. 5 illustrates an example of a training signal included in training data 42 illustrated in FIG. 1. Training signal 43 illustrated in FIG. 5 is an example of a reception signal received by one transceiver in a measurement period.

Training signal 43 illustrated in FIG. 5 has time response waveforms of a plurality of reception signals obtained by transceivers 30A to 30H receiving in advance the reception signals including one or more reflected signals resulting from one or more of the transmission signals transmitted by antenna elements 31A to 31H to known living body 50 (the second living body) which is remaining still in a given position and orientation in predetermined region A1, being reflected by the surface of living body 50. Training signal 43 is stored together with the result of estimation of the position and orientation at the time of measurement. That is to say, training signal 43 illustrated in FIG. 5 includes a plurality of reception signals obtained by transceivers 30A to 30H receiving in advance the reception signals including the reflected signals in a measurement period. Here, the measurement period is a length of time that is K times greater than the predetermined length of time, where K is greater than or equal to two. An example of the measurement period is, but not limited to, 120 [s]. The measurement period may be 3 [s], 10 [s], or 30 [s], so long as it is greater than or equal to the cycle of human heartbeat.

In the manner as described, estimation device 10 can identify living body 50 by circuitry 40 processing the reception signals received by transceivers 30A to 30H.

[Operations of Estimation Device 10]

Figure 6:
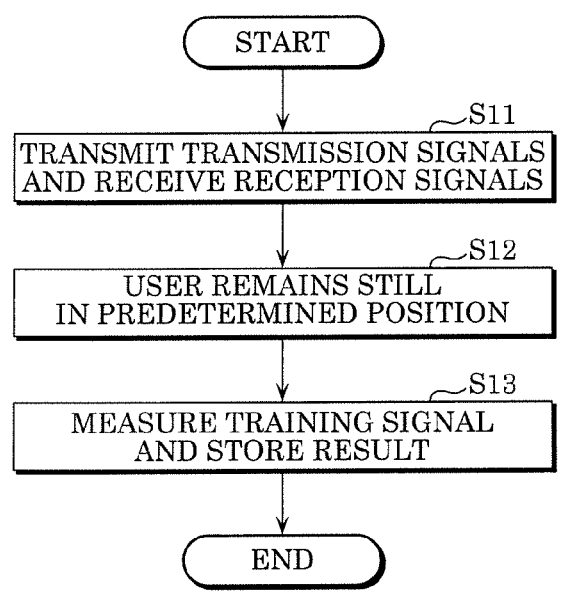
FIG. 6 is a flow chart illustrating an example of initial operations of the estimation device according to Embodiment 1.
Figure 7:
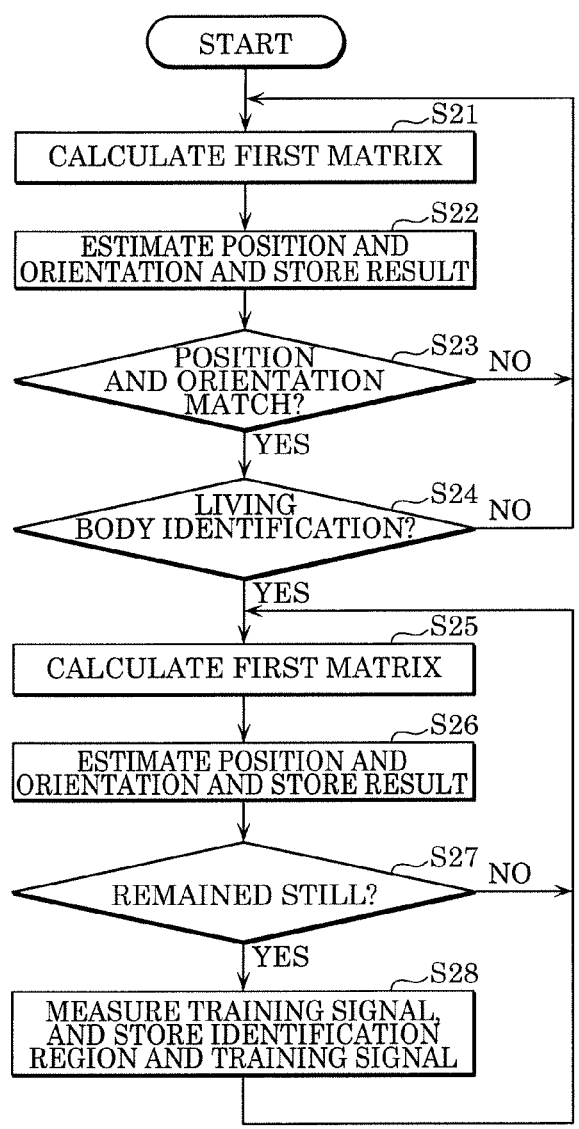
FIG. 7 is a flow chart illustrating an example of operations of the estimation device according to Embodiment 1.

Next, operations of estimation device 10 having the above configuration will be described. FIG. 6 is a flow chart illustrating an example of initial setting operations of estimation device 10 according to the present embodiment. FIG. 7 is a flow chart illustrating an example of operations of estimation device 10 according to the present embodiment.

First, estimation device 10 records a training signal as an initial setting, as illustrated in the flow chart in FIG. 6. More specifically, estimation device 10 transmits first transmission signals to predetermined region A1 in which the first living body is present, using the M transmission antenna elements. Then, each of the N reception antenna elements of estimation device 10 receives, in a predetermined length of time, first reception signals which include one or more reflected signals resulting from one or more of the first transmission signals being reflected by the first living body (S11). For example, transceivers 30A to 30H cause antenna elements 31A to 31H to transmit the transmission signals to predetermined region A1.

Next, estimation device 10 instructs the user, who is the living body, to be still in a predetermined position and a predetermined orientation (S12). For example, as illustrated in FIG. 3, estimation device 10 instructs the user to be still while facing toward TV 70 in position 50A which is the center of predetermined region A1.

With this, estimation device 10 can transmit first transmission signals while the user is still in a predetermined position, and receive, in a predetermined length of time, first reception signals which include one or more reflected signals resulting from one or more of the first transmission signals being reflected by the user. Note that the order in which Step S11 and Step S12 are performed is not limited to the above example; Step S12 may precede Step S11, or Step S11 and Step S12 may be performed in parallel.

Then, using antenna elements 31A to 31H, transceivers 30A to 30H receive, in a predetermined length of time, e.g., 60 seconds, first reception signals which include one or more reflected signals resulting from one or more of the first transmission signals being reflected by the first living body, and circuitry 40 divides the first reception signals by a known signal and stores the result of the division as a training signal in memory 41 (S13). Circuitry 40 also stores, in memory 41, the position (a training position) and the orientation (a training orientation) of the living body, the training signal, and a living body ID (identification information) which is an ID that identifies the living body, in association with one another.

Here, the position and orientation specified for initially obtaining the training signal may be manually set by the user in advance. The training position and training orientation for obtaining the training signal need not be specified by estimation device 10. Estimation unit 411 of estimation device 10 may estimate the position and orientation of the living body, and store the estimated position and orientation in memory 41 as the training position and training orientation.

Next, operations in practical use after obtainment of the training data will be described with reference to FIG. 7.

First, estimation device 10 transmits M transmission signals and receives N reception signals. More specifically, estimation device 10 transmits first transmission signals to predetermined region A1 in which a second living body is present, using the M transmission antenna elements. Then, each of the N reception antenna elements of estimation device 10 receives, in a predetermined length of time, second reception signals which include one or more reflected signals resulting from one or more of the first transmission signals being reflected by the second living body. In the present embodiment, transceivers 30A to 30H cause antenna elements 31A to 31H to transmit transmission signals to predetermined region A1 while the second living body, which is living body 50 to be identified, is located in predetermined region A1. Then, using antenna elements 31A to 31H, transceivers 30A to 30H receive, in a predetermined length of time, the second reception signals which include one or more reflected signals resulting from one or more of the first transmission signals being reflected by the first living body, and first matrix calculator 410 of circuitry 40 calculates a first matrix by dividing the second reception signals by a known signal (S21).

Figure 8:
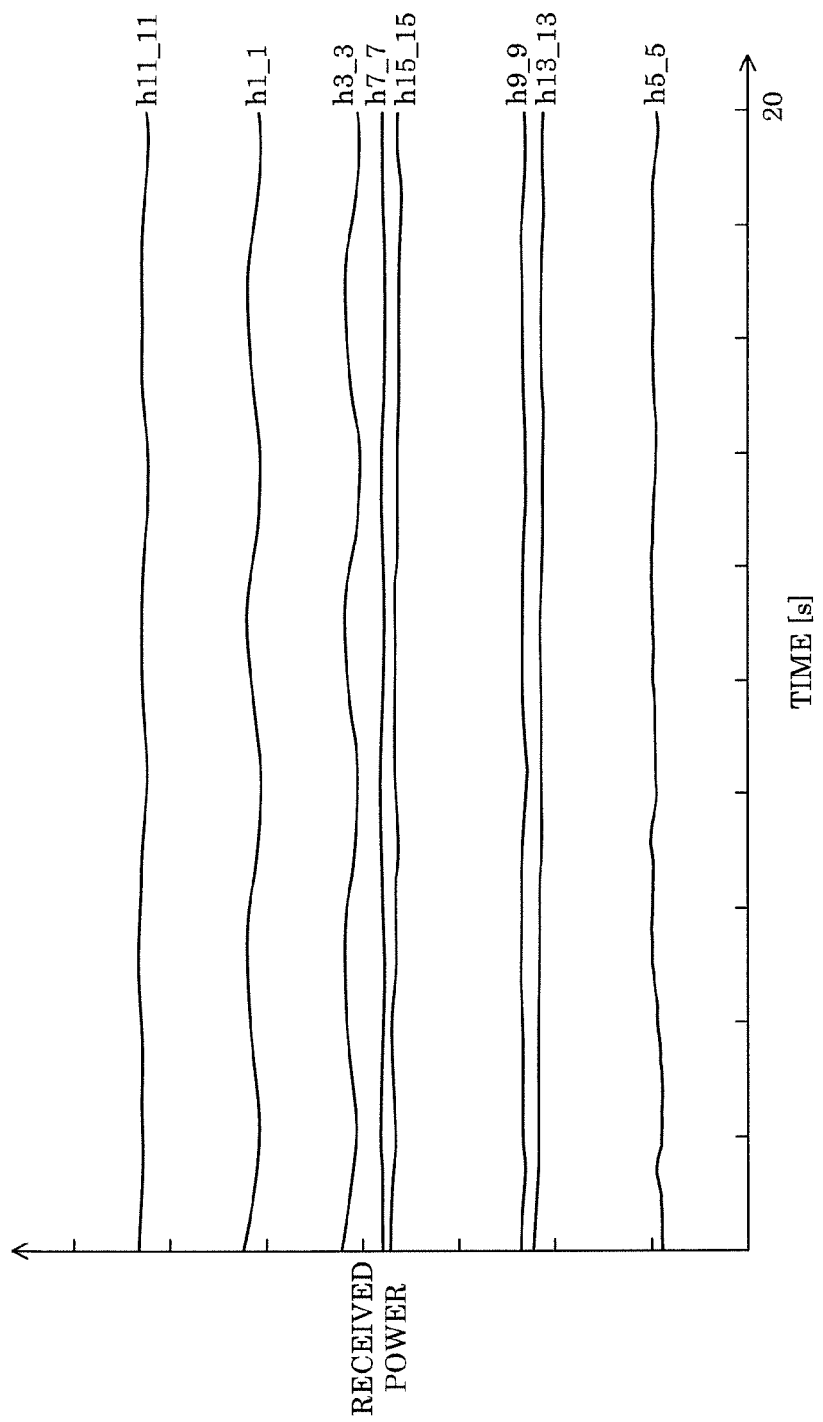
FIG. 8 illustrates an example of propagation channels calculated from reception signals.

FIG. 8 illustrates an example of propagation channels calculated from the reception signals received.

In the identification test illustrated in FIG. 3, for example, a square room of six meters by six meters in a plan view is assumed as predetermined region A1 as described above, and eight transceivers corresponding to transceivers 30A to 30H are disposed around predetermined region A1. The eight transceivers are disposed at the four corners of predetermined region A1 and the centers of the four sides of predetermined region A1. The living body, which is the subject, corresponds to living body 50 to be identified, that is, the first living body. Each of the reception antenna elements and the transmission antenna elements corresponding to antenna elements 31A to 31H is a quadrilateral patch antenna, and is an array antenna of, for example, four antenna elements arranged in the horizontal direction. More specifically, each of 32 reception antenna elements included in the eight transceivers is a quadrilateral patch antenna, and is disposed at the height of 0.9 m from the floor surface. Each of 32 transmission antenna elements included in the eight transceivers is disposed directly above a corresponding reception antenna element by one wavelength of microwaves of the corresponding reception antenna element.

Note that, as illustrated in FIG. 8, it can be seen that component $h_{1\_1}$ and component $h_{3\_3}$ of the propagation channels cyclically exhibit large fluctuations, and have similar waveforms. Component $h_{1\_1}$ and component $h_{3\_3}$ are channel responses of the reception antenna elements located in front of subject 50*a*.

The other components are channel responses of the reception antenna elements located at the rear or the lateral sides of subject 50*a*. That is to say, it can be seen that the fluctuations at the rear and the lateral sides of the living body are small. This is considered to be because the fluctuations caused by organic activity occur in the chest and/or abdomen in the front of the living body.

Next, estimation unit 411 of circuitry 40 in estimation device 10 estimates the position and orientation of the living body using the first matrix calculated by first matrix calculator 410 (S22). More specifically, estimation unit 411 estimates the position and orientation of the living body through, for example, estimation that uses the MUSIC method disclosed in Japanese Unexamined Patent Application Publication No. 2018-8021 or estimation that uses a feature quantity of the first matrix as disclosed in Non-Patent Literature 1.

Next, determination unit 412 of circuitry 40 refers to the training signal, the training position, the training orientation, and the identification information (living body ID) included in training data 42 stored in memory 41, and determines whether the estimated position and the estimated orientation of the living body match the condition of the identification region (S23).

Next, when the living body is determined to match the condition of the identification region in Step S23 (yes in S23), living body identification unit 413 performs living body identification by calculating a correlation between the training signal and the first matrix using the method disclosed in Non-Patent Literature 2 (S24). When the result of the living body identification shows that the living body matches the living body whose living body ID is included in training data 42 (yes in S24), living body identification unit 413 assigns the living body ID associated with the training signal to position data indicating the estimated position of the living body.

Next, when the result of the living body identification shows that the living body matches the living body whose living body ID is included in training data 42 (yes in S24), estimation device 10 continues the calculation of the first matrix and the estimation of the position and orientation of the living body at regular intervals, e.g., 0.5-second intervals. Specifically, Step S25 and Step S26, which correspond to Step S21 and Step S22, respectively, are performed. With this, a newly estimated position of the living body identified in Step S24 is obtained, and a specified living body ID is assigned to position data indicating the newly estimated position. In such a manner, the identified living body is tracked.

Then, using the position data obtained in Steps S25 and S26, determination unit 412 determines whether the living body remains still for the second determination period or longer, e.g., five seconds or longer, under a condition which does not match the condition of the identification region previously stored in memory 41 (S27).

When it is determined in Step S27 that the living body matches the condition of the identification region or that the living body does not remain still for the second determination period or longer (no in S27), the processing returns to Step S25. For example, subsequent Step S27 may be performed 0.5 seconds after previous Step S27. With this, when it is determined "no" in Step S27, Steps S25 to S27 are performed at regular intervals.

Note that Step S25 and Step S26 may be repeated at regular intervals, and using plural items of position data obtained from repeated Step S25 and Step S26, it may be determined in Step S27 whether the living body remains still for five seconds or longer.

Then, when it is determined in Step S27 that the living body has remained still for five seconds or longer under the condition which does not match the condition of the identification region (yes in S27), training data is generated by associating the living body with (i) the position and orientation of the living body when the living body remained still for five seconds or longer and (ii) the first matrix obtained from the reception signals received while the living body remained still, and the generated training data is added to memory 41 (S28).

Living body identification does not start on the living body, i.e., the subject, when the living body enters predetermined region A1 where the living body was previously not present, but starts when the living body remains still while matching the condition of the identification region. When it is determined in the living body identification that the correlation coefficient between the training signal and the first matrix is high and the living body is identical to the living body having the living body ID associated with the training signal, the living body currently subjected to the living body identification is tracked thereafter by estimating the position at regular intervals and associating the estimated positions with the living ID. Further, when the living body is identified and then remains still while not matching the condition of the identification region stored in memory 41, the reception signals obtained in the position and orientation in which the living body remained still are added to the training data in memory 41 together with the position and orientation, as a new identification region. In such a manner, the identification regions that enable identification of the living body can be increased by adding, after the living body identification, identification regions corresponding to the identified living body. Therefore, when the identified living body temporarily moves out of predetermined region A1 during an activity in predetermined region A1, and then returns to predetermined region A1, the living body can be identified easily.

Advantageous Effects Etc

With estimation device 10 according to the present embodiment, the transceivers disposed in, for example, eight positions around predetermined region A1 each transmit transmission waves and receive reception signals. Estimation device 10 then estimates at regular intervals the position and orientation of a living body which enters predetermined region A1, and continues determining whether the estimated position and orientation match the condition of the identification region. Thereafter, estimation device 10 performs living body identification when the estimated position and orientation of the living body satisfy the condition of the identification region, and determines, as a result of the living body identification, whether the living body matches the second living body included in training data 42. Estimation device 10 then estimates the position and orientation of the first living body which is determined to match the second living body in the living body identification, so as to track the first living body. When the first living body remains still under a condition that does not match the condition of the identification region included in training data 42, estimation device 10 determines the position and the orientation in which the first living body remained still as a training position and a training position, respectively, and newly records a first matrix which is calculated from the reception signals obtained when the first living body remained still. This makes it possible to add a new identification region, and increase regions recorded in training data 42 in advance for identifying the first living body. Thus, even when the target region is a relatively large space, it is possible to efficiently re-identify the first living body in the target region.

Note that this living body identification has shown that the success rate for the identification increases with an increase in the total number of antenna elements disposed.

Embodiment 2

In Embodiment 2, the transmission antenna elements and the reception antenna elements are disposed in arrays in the vertical direction as well. The following describes estimation device 10A that estimates the height or the posture of a living body in addition to the position and orientation of the living body, and an estimation method performed by estimation device 10A.

[Configuration of Estimation Device 10A]

Figure 9:
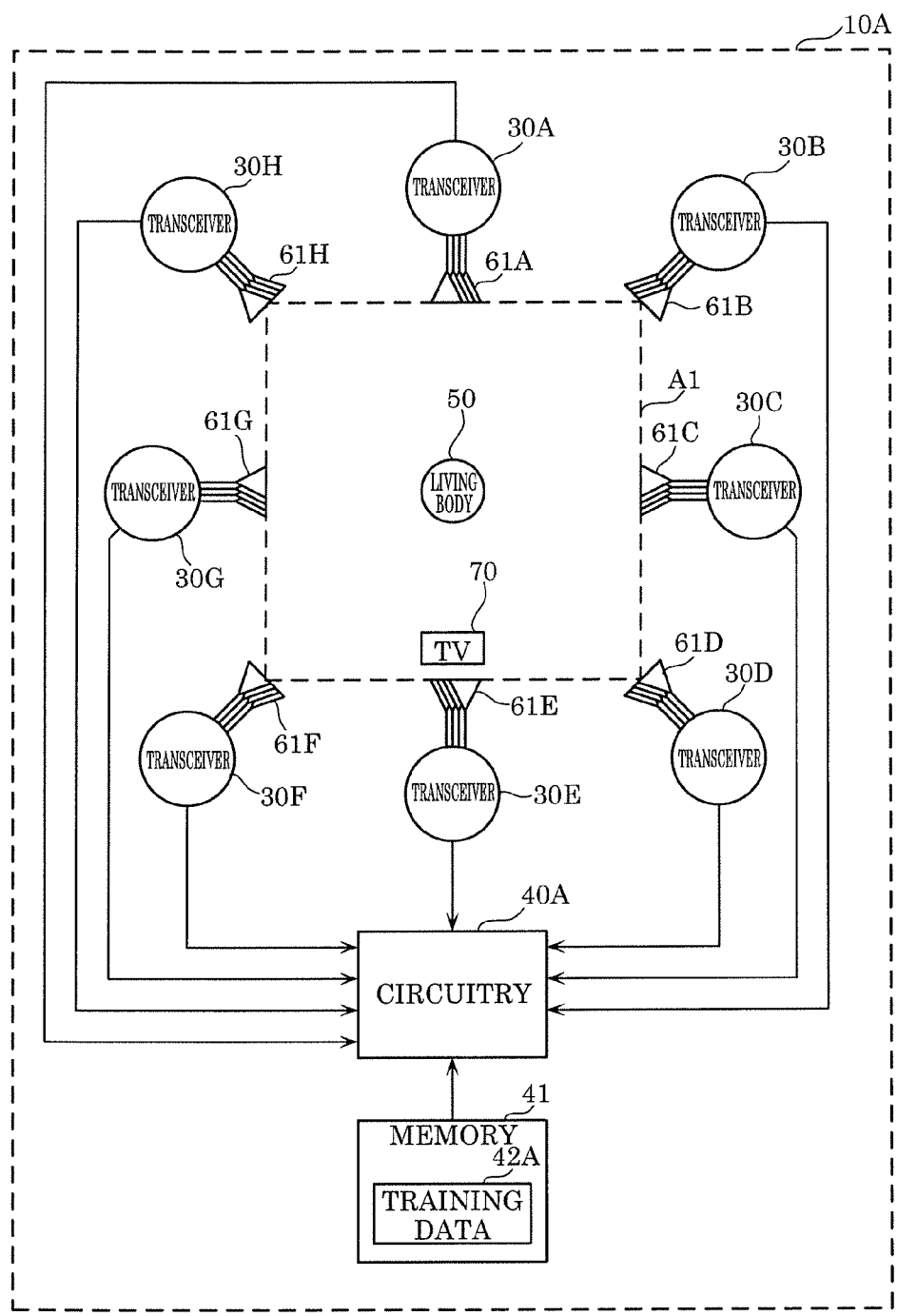
FIG. 9 is a configuration diagram illustrating an example of a configuration of an estimation device according to Embodiment 2.
Figure 10:
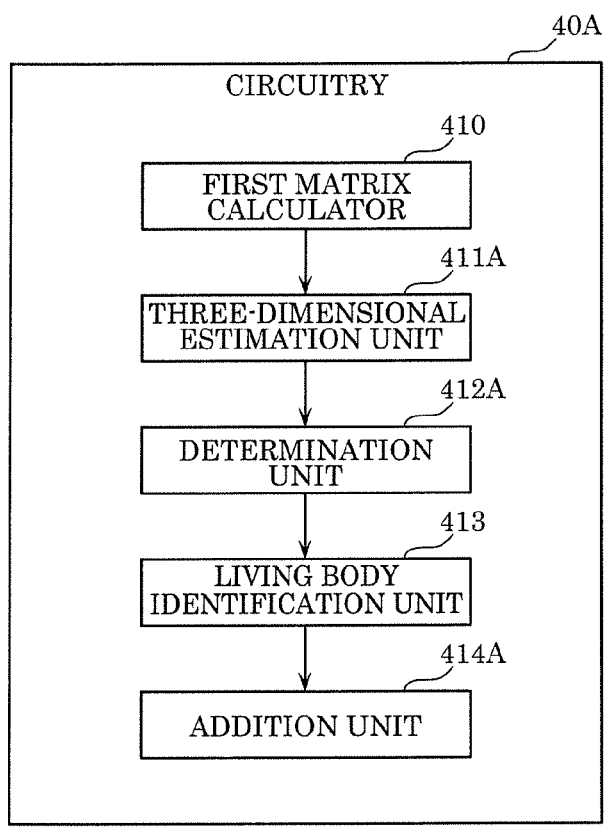
FIG. 10 is a configuration diagram illustrating an example of a detailed configuration of circuitry illustrated in FIG. 9.

FIG. 9 is a block diagram illustrating an example of a configuration of estimation device 10A according to Embodiment 2. FIG. 10 is a configuration diagram illustrating an example of a detailed configuration of circuitry illustrated in FIG. 9. In FIG. 9 and FIG. 10, components that are same as those in FIG. 1 and FIG. 2 are given the same numerical signs, and detailed descriptions are omitted. In Embodiment 2, components that are same as those in Embodiment 1 perform the same operations and have the same variations unless otherwise stated, and overlapping descriptions are omitted.

Estimation device 10A according to Embodiment 2 includes: transceivers 30A to 30H which include antenna elements 61A to 61H, respectively; circuitry 40A; and memory 41.

[Antenna Elements 61A to 61H]

Transceivers 30A to 30H include M antenna elements 61A to 61H, where M is a natural number greater than or equal to two. Transceivers 30A to 30H include array antennas of M antenna elements 61A to 61H that are arranged in a first predetermined direction along the horizontal plane and a second predetermined direction along the vertical plane. In the present embodiment, since transmitters and receivers are integrally formed as transceivers, antenna elements are used as both transmission antenna elements and reception antenna elements; however, transmission antenna elements and reception antenna elements may be disposed separately.

At least three of M transmission antenna elements are disposed in different positions in the vertical and horizontal directions. Furthermore, at least three of N reception antenna elements are disposed in different positions in the vertical and horizontal directions.

[Circuitry 40A]

As circuitry 40A has the same hardware configuration as circuitry 40, the description thereof is omitted. The function configuration of circuitry 40A is different from that of circuitry 40. Specifically, circuitry 40A includes three-dimensional estimation unit 411A, determination unit 412A, and addition unit 414A instead of estimation unit 411, determination unit 412, and addition unit 414. As first matrix calculator 410 and living body identification unit 413 are the same as those in circuitry 40, the descriptions thereof are omitted.

<Three-Dimensional Estimation Unit 411A>

By adopting antenna elements 61A to 61H as the transmission antennas and reception antennas, three-dimensional estimation unit 411A estimates, in addition to the position and orientation of the living body, the position of the living body in the height direction and the posture of the living body, using a method disclosed in Japanese Unexamined Patent Application Publication No. 2018-8021.

Specifically, using the calculated first matrix, three-dimensional estimation unit 411A successively estimates combinations each of which is a combination of a three-dimensional position and an orientation of the first living body relative to the estimation device, in a time series that is the order in which the N reception signals are received. A three-dimensional position includes, in addition to a two-dimensional position in a plan view, a vertical position of the first living body in the vertical direction.

Moreover, three-dimensional estimation unit 411A successively calculates, for each of the successively estimated three-dimensional positions, an RCS value corresponding to the first living body based on the three-dimensional position, the positions of the transmission antenna elements, and the positions of the reception antenna elements. Three-dimensional estimation unit 411A then successively estimates the posture of the first living body for each combination, using a change over time in the successively estimated three-dimensional positions, a change over time in the successively estimated RCS values, and information indicating correspondence stored in memory 41.

Note that the information indicating correspondence is information in which (i) a change over time in the vertical position of the first living body, that is, the position of the first living body in the vertical direction relative to estimation device 10A, (ii) a change over time in the RCS values, and (iii) an action of the first living body, are associated with one another. The information indicating correspondence is information indicating a range of RCS value and a range of height that are associated in advance with each posture including lying on the back, sitting cross-legged, sitting in a seat, and standing upright. For example, lying on the back is associated with a first RCS range and a first height range, sitting cross-legged is associated with a second RCS range and a second height range, sitting in a seat is associated with a third RCS range and a third height range, and standing upright is associated with a fourth RCS range and a fourth height range. Note that the first RCS range through the fourth RCS range are different ranges of RCS value. The first height range through the fourth height range are different ranges of height.

<Determination Unit 412A>

Determination unit 412A determines whether (i) the three-dimensional position in the estimated combination is in a first identification region which is included in predetermined region A1 and stored in memory 41 in advance as an identification region, (ii) the orientation of the first living body in the combination is in a predetermined range relative to a first direction stored in memory 41 in advance, and (iii) the posture of the first living body in the combination matches a first posture stored in memory 41 in advance. Specifically, determination unit 412A refers to the first identification region included in training data 42A stored in memory 41, to refer to a first training position, a first training orientation, and a first training posture of a living body that are associated with a first training signal in the first identification region referred to. Here, the first identification region is information in which (i) the first training signal, (ii) the first training position, the first training orientation, and the first training posture which are the position, orientation, and posture of the living body at the time of reception of the first training signal, respectively, and (iii) identification information that identifies the living body, are associated with one another. As illustrated in FIG. 11, training data 42A stored in memory 41 is different from training data 42 according to Embodiment 1 in that a training posture is included in addition to a training position and a training orientation. FIG. 11 illustrates an example of training data stored in the memory according to Embodiment 2.

In such a manner as described above, determination unit 412A determines whether the living body satisfies the condition of the identification region not only based on the estimated position and orientation but also the estimated posture, on the basis of the result of estimation by three-dimensional estimation unit 411A. More specifically, determination unit 412A not only determines whether the position and orientation of the living body match the condition at the time of obtaining the training data, but also determines whether the posture of the living body such as standing, sitting, or lying on the back matches the condition at the time of obtaining the training data.

<Living Body Identification Unit 413>

As with living body identification unit 413 according to Embodiment 1, when determination unit 412A determines that the living body satisfies the condition of the first identification region, living body identification unit 413 performs living body identification based on time waveforms of the reception signals and the first training signal corresponding to the living body obtained in advance under the condition of the first identification region, using a method etc. disclosed in Non-Patent Literature 2, for example. The condition of the first identification region is that (i) the three-dimensional position of the first living body in the estimated combination is in the first identification region, (ii) the orientation of the first living body in the combination is in a predetermined range, and (iii) the posture of the first living body in the combination matches a first posture.

<Addition Unit 414A>

Apart from the conditions for the determination by addition unit 414 according to Embodiment 1, addition unit 414A performs the determination based on the posture of the living body as well. Addition unit 414A adds, as the identification region for identifying the first living body identified, a new identification region which is based on information indicating an estimated next position of the first living body identified. With this, a new second identification region is added to training data 42A in memory 41 as the identification region for identifying the first living body. Specifically, once the living body identification is performed on the living body by living body identification unit 413, living body addition unit 414A continues tracking the living body based on plural estimation results obtained by three-dimensional estimation unit 411A at regular intervals, e.g., 0.5-second intervals.

Furthermore, when the living body remains still for a second determination period or longer under the condition of the second identification region different from the first identification region, addition unit 414A generates a second training signal corresponding to the second identification region based on (i) the reception signals received in the second determination period and (ii) a second training position, a second training orientation, and a second training posture which are the position, orientation, and posture of the living body estimated using the reception signals. The second training signal has a waveform different from the waveform of the first training signal. Specifically, addition unit 414A performs processing using the result of determination by determination unit 412A indicating whether the living body has remained still for the second determination period or longer, e.g., five seconds or longer, in a position, an orientation, and a posture different from at least one of the first training position, the first training orientation, and the first training posture that serve as the standard for the condition of the first identification region. When the living body which has undergone the living body identification has remained still in the above-described position, orientation, posture for the second determination period or longer, addition unit 414A determines the position as a second training position, the orientation as a second training orientation, and the posture as a second training posture, and generates second training data by associating the living body with the second training position, the second training orientation, the second training posture, and the second training signal which includes the reception signals obtained in the second determination period.

With this, next time when the first living body is to be identified, in the case where the first living body is estimated to have remained still for a predetermined period or longer under the condition of the first identification region or the second identification region based on the result of estimation by estimation unit 411, living body identification unit 413 can identify the first living body based on (i) the time waveforms of the reception signals and (ii) the first training signal and the second training signal which are obtained in advance under the condition of the first identification region or the second identification region and which correspond to the second living body.

[Operations of Estimation Device 10A]

Figure 12:
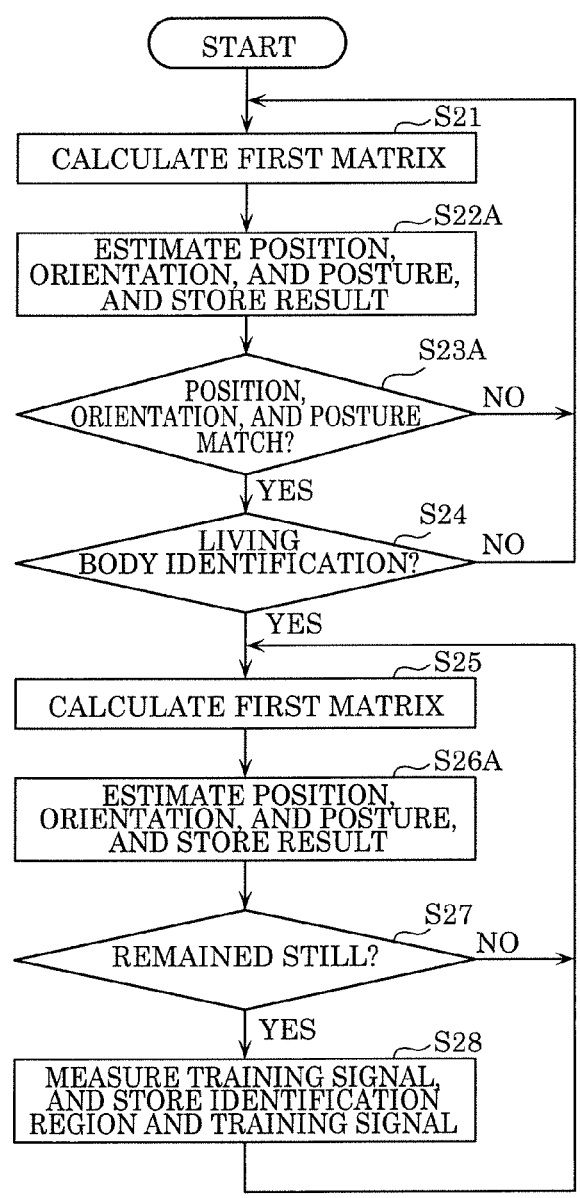
FIG. 12 is a flow chart illustrating an example of operations of the estimation device according to Embodiment 2.

Next, operations of estimation device 10A having the above configuration will be described. FIG. 12 is a flow chart illustrating an example of operations of estimation device 10A according to Embodiment 2. In FIG. 12, the operations that are same as those in the flow chart according to Embodiment 1 are given the same numerical signs, and detailed descriptions are omitted.

After Step S21, three-dimensional estimation unit 411A of circuitry 40A in estimation device 10A estimates the position, orientation, and posture of the living body using the first matrix calculated by first matrix calculator 410 (S22A). Since each of antenna elements 61A to 61H of estimation device 10A consists of a plurality of antenna elements disposed in an array in the horizontal direction and the vertical direction, it is possible to estimate the height and posture of the living body in addition to the position and orientation of the living body.

Next, determination unit 412A of circuitry 40A refers to the training signal, the training position, the training orientation, the training posture, and the identification information (living body ID) included in training data 42A stored in memory 41, and determines whether the estimated three-dimensional position, orientation, and posture of the living body match the condition of the identification region (S23A).

Furthermore, after the living body identification of the living body in Step S24, when the living body is determined to match the living body whose living body ID is included in training data 42A, estimation device 10A continues the calculation of the first matrix and the estimation of the three-dimensional position, orientation, and posture of the living body at regular intervals, e.g., 0.5-second intervals. Specifically, Step S25 and Step S26A, which correspond to Step S21 and Step S22A, respectively, are performed. With this, a newly estimated three-dimensional position of the living body identified in Step S24 is obtained, and a specified living body ID is assigned to position data indicating the newly estimated three-dimensional position. In such a manner, the identified living body is tracked.

Then, using the position data obtained in Steps S25 and S26A, determination unit 412A determines whether the living body remains still for the second determination period or longer, e.g., five seconds or longer, under a condition which does not match the condition of the identification region previously stored in memory 41 (S27).

When it is determined in Step S27 that the living body matches the condition of the identification region or that the living body does not remain still for the second determination period or longer (no in S27), the processing returns to Step S25. For example, subsequent Step S27 may be performed 0.5 seconds after previous Step S27. With this, when it is determined "no" in Step S27, Steps S25 to S27 are performed at regular intervals.

Note that Step S25 and Step S26A may be repeated at regular intervals, and using plural items of position data obtained from repeated Step S25 and Step S26A, it may be determined in Step S27 whether the living body remains still for five seconds or longer.

Then, when it is determined in Step S27 that the living body has remained still for the second determination period or longer (five seconds or longer) under the condition which does not match the condition of the identification region (yes in S27), training data is generated by associating the living body with (i) the three-dimensional position, orientation, and posture of the living body when the living body remained still for five seconds or longer and (ii) the first matrix obtained from the reception signals received while the living body remained still, and the generated training data is added to memory 41 (S28).

Advantageous Effects Etc

With estimation device 10A according to the present embodiment, the transceivers disposed in, for example, eight positions around predetermined region A1 each transmit transmission waves and receive reception signals. Estimation device 10A then estimates at regular intervals the three-dimensional position, orientation, and posture of a living body which enters predetermined region A1, and continues determining whether the estimated position, orientation, and posture match the condition of the identification region. Thereafter, estimation device 10A performs living body identification when the estimated position, orientation, and posture of the living body satisfy the condition of the identification region, and determines, as a result of the living body identification, whether the living body matches the second living body included in training data 42A. Estimation device 10A then estimates the position, orientation, and posture of the first living body which is determined to match the second living body in the living body identification, so as to track the first living body. When the first living body remains still under a condition that does not match the condition of the identification region included in training data 42A, estimation device 10A determines the position, orientation, and posture in which the first living body remained still as a training position, a training position, and a training posture, respectively, and newly records a first matrix which is calculated from the reception signals obtained when the first living body remained still. This makes it possible to add a new identification region, and increase regions recorded in training data 42A in advance for identifying the first living body. Thus, even when the target region is a relatively large space, it is possible to efficiently re-identify the first living body in the target region.

Note that each component of the above-described embodiments may be implemented by a dedicated hardware product or by execution of a software program appropriate for the component. Each component may also be implemented by reading and executing, by a program execution unit such as a central processing unit (CPU) or a processor, a software program recorded on a recording medium such as a hard disk or semiconductor memory. Here, software that implements the estimation device etc. according to the above-described embodiments is a program as follows:

The program causes a computer to execute an estimation method for an estimation device which includes an antenna and memory, the antenna including M transmission antenna elements and N reception antenna elements, where M and N are each a natural number greater than or equal to two. The estimation method includes: transmitting transmission signals to a target region using the M transmission antenna elements; receiving, by the N reception antenna elements, reception signals which include one or more reflected signals resulting from one or more of the transmission signals transmitted by the M transmission antenna elements being reflected by a first living body; calculating, from N reception signals respectively received by the N reception antenna elements in a predetermined length of time, an M×N first matrix whose components are complex transfer functions each indicating a propagation characteristic between one of the M transmission antenna elements and one of the N reception antenna elements; successively estimating, using the first matrix calculated, combinations each of which is a combination of a position and an orientation of the first living body relative to the estimation device, in a time series that is an order in which the N reception signals are received; determining, for each of the combinations successively estimated, whether (i) the position of the first living body in the combination is in a first identification region which is included in the target region and stored in the memory in advance as an identification region and (ii) the orientation of the first living body in the combination is in a predetermined range relative to a direction stored in the memory in advance; identifying the first living body based on time waveforms of the reception signals and a first training signal which is obtained in advance in the first identification region and corresponds to a second living body, when (i) the position of the first living body in the combination is included in the first identification region and (ii) the orientation of the first living body in the combination is in the predetermined range; and adding a new identification region as the identification region for identifying the first living body identified, the new identification region being based on information indicating an estimated next position of the first living body identified.

Moreover, the program causes a computer to execute an estimation method for an estimation device which includes an antenna and memory, the antenna including M transmission antenna elements and N reception antenna elements, where M and N are each greater than or equal to three. The memory stores information indicating correspondence among (i) a change over time in a vertical position of the first living body in a vertical direction relative to the estimation device, (ii) a change over time in a radar cross-section (RCS) value, and (iii) an action of a first living body. The M transmission antenna elements include at least three transmission antenna elements disposed in different positions in the vertical direction and a horizontal direction. The N reception antenna elements include at least three reception antenna elements disposed in different positions in the vertical direction and the horizontal direction. The estimation method includes: transmitting transmission signals to a target region using the M transmission antenna elements; receiving, by the N reception antenna elements, reception signals which include one or more reflected signals resulting from one or more of the transmission signals transmitted by the M transmission antenna elements being reflected by a first living body; calculating, from N reception signals respectively received by the N reception antenna elements in a predetermined length of time, an M×N first matrix whose components are complex transfer functions each indicating a propagation characteristic between one of the M transmission antenna elements and one of the N reception antenna elements; successively estimating, using the first matrix calculated, combinations each of which is a combination of a three-dimensional position and an orientation of the first living body relative to the estimation device, in a time series that is an order in which the N reception signals are received, the three-dimensional position including the vertical position; successively calculating, for each of three-dimensional positions successively estimated, an RCS value corresponding to the first living body based on the three-dimensional position, positions of the M transmission antenna elements, and positions of the N reception antenna elements; successively estimating a posture of the first living body for each of the combinations, using (i) a change over time in the three-dimensional positions successively estimated, (ii) a change over time in RCS values successively calculated, and (iii) the information indicating the correspondence stored in the memory; determining, for each of the combinations successively estimated, whether (i) the three-dimensional position in the combination is in a first identification region which is included in the target region and stored in the memory in advance as an identification region, (ii) the orientation of the first living body in the combination is in a predetermined range relative to a first direction stored in the memory in advance, and (iii) the posture of the first living body in the combination matches a first posture stored in the memory in advance; identifying the first living body based on time waveforms of the reception signals and a first training signal which is obtained in advance in the first identification region and corresponds to a second living body, when (i) the three-dimensional position of the first living body in the combination is in the first identification region, (ii) the orientation of the first living body in the combination is in the predetermined range, and (iii) the posture of the first living body in the combination matches the first posture; and adding a new identification region as the identification region for identifying the first living body identified, the new identification region being based on information indicating an estimated next position of the first living body identified.

While the foregoing has described estimation devices 10 and 10A according to one or more aspects of the present disclosure based on exemplary embodiments, the present disclosure is not limited to the exemplary embodiments. Various modifications to these embodiments conceivable to those skilled in the art, as well as embodiments resulting from combinations of components in different embodiments may be included within the scope of one or more aspects of the present disclosure, so long as they do not depart from the essence of the present disclosure.

Although only some exemplary embodiments of the present disclosure have been described in detail above, those skilled in the art will readily appreciate that many modifications are possible in the exemplary embodiments without materially departing from the novel teachings and advantages of the present disclosure. Accordingly, all such modifications are intended to be included within the scope of the present disclosure.

INDUSTRIAL APPLICABILITY

The present disclosure is applicable to an estimation device and an estimation method for identifying a living body using radio signals, and is particularly applicable to an estimation device and an estimation method used in, for example, home electric appliances that perform control according to a living body and monitoring devices that detect entry of a living body.

What is claimed is:
1. An estimation method for an estimation device which includes an antenna and memory, the antenna including M transmission antenna elements and N reception antenna elements, where M and N are each a natural number greater than or equal to number two, the estimation method comprising:
transmitting transmission signals to a target region using the M transmission antenna elements;

receiving, by the N reception antenna elements, reception signals which include one or more reflected signals resulting from one or more of the transmission signals transmitted by the M transmission antenna elements being reflected by a first living body;

calculating, from N reception signals respectively received by the N reception antenna elements in a predetermined length of time, an M×N first matrix whose components are complex transfer functions each indicating a propagation characteristic between one of the M transmission antenna elements and one of the N reception antenna elements;

successively estimating, using the first matrix calculated, combinations each of which is a combination of a position and an orientation of the first living body relative to the estimation device, in a time series that is an order in which the N reception signals are received;

determining, for each of the combinations successively estimated, whether (i) the position of the first living body in the combination is in a first identification region which is included in the target region and stored in the memory in advance as an identification region and (ii) the orientation of the first living body in the combination is in a predetermined range relative to a direction stored in the memory in advance;

identifying the first living body based on time waveforms of the reception signals and a first training signal which is obtained in advance in the first identification region and corresponds to a second living body, when:
(i) the position of the first living body in the combination is included in the first identification region, and
(ii) the orientation of the first living body in the combination is in the predetermined range; and adding a new identification region as the identification region for identifying the first living body identified, the new identification region being based on information indicating an estimated next position of the first living body identified.

2. The estimation method according to claim 1, wherein the adding of the new identification region includes:
(i) continuing to track, at predetermined time intervals, the position of the first living body identified, based on a result of the estimating;
(ii) when the first living body remains still for a predetermined period or longer in a second identification region different from the first identification region, generating a second training signal corresponding to the second identification region based on reception signals received in the predetermined period and a position and an orientation of the first living body estimated using the reception signals; and
(iii) adding the second training signal as a training signal for identifying, in the second identification region, the first living body identified, and
in the identifying of the first living body, the first living body in the first identification region is identified using the first training signal, and the first living body in the second identification region is identified using the second training signal.

3. The estimation method according to claim 2, further comprising:
identifying the first living body based on:
time waveforms of the reception signals, and
the first training signal and the second training signal which are obtained in advance in the first identification region or the second identification region and correspond to a second living body,
when the first living body is estimated to have remained still for the predetermined period or longer in the first identification region or the second identification region based on the result of the estimating.

4. An estimation method for an estimation device which includes an antenna and memory, the antenna including M transmission antenna elements and N reception antenna elements, where M and N are each greater than or equal to number three,
the memory storing information indicating correspondence among:
(i) a change over time in a vertical position of a first living body in a vertical direction relative to the estimation device,
(ii) a change over time in a radar cross-section (RCS) value, and
(iii) an action of a first living body,
the M transmission antenna elements including at least three transmission antenna elements disposed in different positions in the vertical direction and a horizontal direction,
the N reception antenna elements including at least three reception antenna elements disposed in different positions in the vertical direction and the horizontal direction,
the estimation method comprising:
transmitting transmission signals to a target region using the M transmission antenna elements;
receiving, by the N reception antenna elements, reception signals which include one or more reflected signals resulting from one or more of the transmission signals transmitted by the M transmission antenna elements being reflected by a first living body;
calculating, from N reception signals respectively received by the N reception antenna elements in a predetermined length of time, an M×N first matrix whose components are complex transfer functions each indicating a propagation characteristic between one of the M transmission antenna elements and one of the N reception antenna elements;
successively estimating, using the first matrix calculated, combinations each of which is a combination of a three-dimensional position and an orientation of the first living body relative to the estimation device, in a time series that is an order in which the N reception signals are received, the three-dimensional position including the vertical position;
successively calculating, for each of three-dimensional positions successively estimated, an RCS value corresponding to the first living body based on the three-dimensional position, positions of the M transmission antenna elements, and positions of the N reception antenna elements;
successively estimating a posture of the first living body for each of the combinations, using:
(i) a change over time in the three-dimensional positions successively estimated,
(ii) a change over time in RCS values successively calculated, and
(iii) the information indicating the correspondence stored in the memory;
determining, for each of the combinations successively estimated, whether:

(i) the three-dimensional position in the combination is in a first identification region which is included in the target region and stored in the memory in advance as an identification region, (ii) the orientation of the first living body in the combination is in a predetermined range relative to a first direction stored in the memory in advance, and (iii) the posture of the first living body in the combination matches a first posture stored in the memory in advance;

identifying the first living body based on time waveforms of the reception signals and a first training signal which is obtained in advance in the first identification region and corresponds to a second living body, when:

(i) the three-dimensional position of the first living body in the combination is in the first identification region, (ii) the orientation of the first living body in the combination is in the predetermined range, and (iii) the posture of the first living body in the combination matches the first posture; and adding a new identification region as the identification region for identifying the first living body identified, the new identification region being based on information indicating an estimated next position of the first living body identified.

5. The estimation method according to claim 4, wherein the adding of the new identification region includes:

(i) continuing to track, at predetermined time intervals, a position of the first living body identified, based on a result of the estimating;

(ii) when the first living body remains still for a predetermined period or longer in at least one second identification region different from the first identification region, generating a second training signal corresponding to the at least one second identification region based on the reception signals received in the predetermined period and a three-dimensional position, an orientation, and a posture of the first living body estimated using the reception signals; and (iii) storing the second training signal in the memory as a training signal for identifying, in the at least one second identification region, the first living body identified, and in the identifying of the first living body, the first living body in the first identification region is identified using the first training signal, and the first living body in the at least one second identification region is identified using the second training signal.

6. The estimation method according to claim 5, further comprising:

identifying the first living body based on:
the time waveforms of the reception signals, and
the first training signal and the second training signal which are obtained in advance in the first identification region or the at least one second identification region and correspond to a second living body,
when the first living body is estimated to have remained still for the predetermined period or longer in the first identification region or the second identification region based on the result of the estimating.

7. An estimation device, comprising:
memory;
an antenna including M transmission antenna elements and N reception antenna elements, where M and N are each greater than or equal to number two;

a transmitter which transmits transmission signals to a target region using the M transmission antenna elements;

a receiver which receives, using the N reception antenna elements, reception signals which include one or more reflected signals resulting from one or more of the transmission signals transmitted by the M transmission antenna elements being reflected by a first living body;

a first matrix calculator which calculates, from N reception signals respectively received by the N reception antenna elements in a predetermined length of time, an M×N first matrix whose components are complex transfer functions each indicating a propagation characteristic between one of the M transmission antenna elements and one of the N reception antenna elements;

an estimation unit configured to successively estimate, using the first matrix calculated, combinations each of which is a combination of a position and an orientation of the first living body relative to the estimation device, in a time series that is an order in which the N reception signals are received;

a determination unit configured to determine, for each of the combinations successively estimated, whether:

(i) the position of the first living body in the combination is in a first identification region which is included in the target region and stored in the memory in advance as an identification region, and (ii) the orientation of the first living body in the combination is in a predetermined range relative to a direction stored in the memory in advance;

a living body identification unit configured to identify the first living body based on time waveforms of the reception signals and a first training signal which is obtained in advance in the first identification region and corresponds to a second living body, when:

(i) the position of the first living body in the combination is in the first identification region, and (ii) the orientation of the first living body in the combination is in the predetermined range; and an addition unit configured to add a new identification region in the memory as the identification region for identifying the first living body identified, the new identification region being based on an estimated next position of the first living body identified.

8. A non-transitory computer-readable recording medium for use in a computer, the recording medium having a computer program recorded thereon for causing the computer to execute an estimation method for an estimation device which includes an antenna and memory, the antenna including M transmission antenna elements and N reception antenna elements, where M and N are each a natural number greater than or equal to number two, the estimation method comprising:

transmitting transmission signals to a target region using the M transmission antenna elements;

receiving, by the N reception antenna elements, reception signals which include one or more reflected signals resulting from one or more of the transmission signals transmitted by the M transmission antenna elements being reflected by a first living body;

calculating, from N reception signals respectively received by the N reception antenna elements in a predetermined length of time, an M×N first matrix whose components are complex transfer functions each indicating a propagation characteristic between one of the M transmission antenna elements and one of the N reception antenna elements;

successively estimating, using the first matrix calculated, combinations each of which is a combination of a position and an orientation of the first living body relative to the estimation device, in a time series that is an order in which the N reception signals are received;
determining, for each of the combinations successively estimated, whether:
(i) the position of the first living body in the combination is in a first identification region which is included in the target region and stored in the memory in advance as an identification region, and
(ii) the orientation of the first living body in the combination is in a predetermined range relative to a direction stored in the memory in advance;
identifying the first living body based on time waveforms of the reception signals and a first training signal which is obtained in advance in the first identification region and corresponds to a second living body, when:
(i) the position of the first living body in the combination is included in the first identification region, and
(ii) the orientation of the first living body in the combination is in the predetermined range; and
adding a new identification region as the identification region for identifying the first living body identified, the new identification region being based on an estimated next position of the first living body identified.

* * * * *